United States Patent [19]

Gozzo et al.

[11] Patent Number: 4,748,284

[45] Date of Patent: May 31, 1988

[54] PROCESS FOR PREPARING 1,1-DIHALO-1,2,2,2-TETRAFLUOROE-THANES

[75] Inventors: Franco Gozzo, San Donato Milanese; Nicola Troiani; Paolo Piccardi, both of Milan, all of Italy

[73] Assignee: Montedison S.p.A., Milan, Italy

[21] Appl. No.: 943,898

[22] Filed: Dec. 19, 1986

Related U.S. Application Data

[63] Continuation of Ser. No. 700,500, Feb. 11, 1985, abandoned, which is a continuation of Ser. No. 435,365, Oct. 20, 1982, abandoned.

[30] Foreign Application Priority Data

Oct. 21, 1981 [IT] Italy ............................. 24602 A/81

[51] Int. Cl.[4] ...................... C07C 17/20; C07C 17/00; C07C 19/08
[52] U.S. Cl. .................................. 570/151; 570/134; 570/137
[58] Field of Search ...................... 570/151, 137, 134

[56] References Cited

U.S. PATENT DOCUMENTS

| | | | |
|---|---|---|---|
| 2,598,411 | 5/1952 | Miller et al. | 570/151 |
| 2,971,990 | 2/1961 | Larsen | 570/137 |
| 3,087,974 | 4/1963 | Hauptschein et al. | 570/151 |
| 3,818,229 | 6/1974 | Long | 570/137 |

FOREIGN PATENT DOCUMENTS 121710 10/1978 Japan ................................. 570/151

OTHER PUBLICATIONS

Okuhara, J. Org. Chem. (1978), 43(14), 2745-9 (Gov. Ind. Res. Inst. Nagoya, Japan).

*Primary Examiner*—J. E. Evans
*Attorney, Agent, or Firm*—Stevens, Davis, Miller & Mosher

[57] ABSTRACT

A process for preparing 1,1-dihalo-1,2,2,2-tetrafluoroethanes by isomerization of 1,2-dihalotetrafluoroethanes at their reflux temperature, by using, as a catalyst, the reaction product prepared "in situ" from an anhydrous aluminum halide with at least equimolecular amounts of the isomer, 1,1-dihalo-1,2,2,2-tetrafluoroethane in a medium consisting of 1,2-dihalotetrafluoroethane. The products find application as intermediates for pyrethroid insecticides.

1 Claim, No Drawings

PROCESS FOR PREPARING 1,1-DIHALO-1,2,2,2-TETRAFLUOROETHANES

This application is a continuation of application Ser. No. 700,500, filed 2-11-85 which in turn is a continuation of Ser. No. 435,365 filed 10-20-82, both now abandoned.

BACKGROUND OF THE INVENTION

The invention relates to a process for preparing 1,1-dihalo-1,2,2,2-tetrafluoroethanes by isomerization of 1,2-dihalotetrafluoroethanes, catalyzed by active complexes obtained "in situ" from aluminium halides, in particular from aluminium bromide or chloride. It is known, for example from M. Hudlicky, Chemistry of Organic Fluorine Comp., 2nd Ed., John Wiley, 501–2 (1976), that fluororalkanes such as $CFCl_2$—$CCl_2F$, $CF_2Cl$—$CCl_2F$, $CF_2Br$—$CHClF$, $CF_2Br$—$CFClBr$, $CF_2Cl$—$CHFI$, may undergo a molecular re-arrangement reaction catalyzed by aluminium halides.

However, the isomerization of 1,2-dihalotetrafluoroethanes into the corresponding asymmetric compounds 1,1-dihalo-1,2,2,2-tetrafluoroethanes has not been described so far.

It is only known, from D. J. Burton and L. J. Kehoe, J.O.C. 35, No. 5, 1339–41 (1970), that 1,2-dibromotetrafluoroethane undergoes a dismutation by treatment with anhydrous aluminium chloride, under reflux conditions, leading to $CF_3$—$CBr_3$, evidently accompanied by an equivalent amount of $CF_3$—$CF_2Br$.

Actually, we have ascertained that anhydrous aluminium chloride, when brought into contact with $CF_2Br$—$CF_2Br$, does not promote the isomerization thereof, even if the reaction mixture is heated at reflux for many hours.

On the other hand, when employing, as a catalyst for isomerizing $CF_2Br$—$CF_2Br$, anhydrous aluminium bromide, which is generally known as the most efficient out of the two Lewis acids, we have observed that the reaction which develops is not reproducible, involves long and too variable induction times and has a non-controllable trend.

In particular we have ascertained that, if the contact between anhydrous $AlBr_3$ and $CF_2Br$—$CF_2Br$ is accomplished at room temperature, no reaction occurs in a time-period of a few hours, while after one or more days $CF_2Br$—$CF_2Br$ results, in many tests, to be completely dismutated with formation of $CF_3$—$CBr_3$ as a solid residue.

Conversely, if the reaction mixture is brought to and maintained under reflux conditions, after highly variable induction times, from 4 hours to many hours, a very intense reaction sets in, which has a non-controllable trend, with forming of variable amounts of isomer $CF_3$—$CFBr_2$ accompanied by amounts of $CF_3$—$CBr_3$ and of $C_2F_5Br$ gradually increasing as the reaction proceeds.

This non-reproducible trend is particularly dangerous when the reaction is accomplished on a scale higher than 10 Kg, as the high exothermy involved could lead to a violent course of the reaction with overflow of material from the cooler.

In no case have we succeeded in obtaining a $CF_3$—$CFBr_2$ yield higher than 70%.

Therefore, a method of preparing, on a commercial scale, $CF_3$—$CFBr_2$ by isomerization of $CF_2Br$—$CF_2Br$, reproducible and controllable in sufficiently safe conditions, was neither available nor inferable from the prior art.

OBJECTS OF THE INVENTION

It has now been found that it is possible to obtain, on a commercial scale, 1,1-dihalo-1,2,2,2-tetrafluoroethanes, in particular $CF_3$—$CFBr_2$, by isomerization of 1,2-dihalotetrafluoroethanes, in particular of 1,2-dibromotetrafluoroethane, under reproducible conditions, under short reaction times, with a complete control of the reaction course, as well as with high yields and very low costs, by employing, as an isomerization catalyst, the reaction product of an aluminium halide with at least equimolecular amounts of 1,1-dihalo-1,2,2,2-tetrafluoroethane, in a medium consisting of said 1,2-dihalotetrafluoroethane to be isomerized.

The isomerization products, obtained by the process of the present invention, and in particular 1,1-dibromo-1,2,2,2-tetrafluoroethane, prove to be useful as starting compounds for the synthesis of new pyrethroid insecticides, according to processes described for example in British patent No. 2,015,519 in the name of Montedison, S.P.A.

GENERAL DESCRIPTION OF THE INVENTION

Thus, it is the object of the present invention to provide a process for preparing 1,1-dihalo-1,2,2,2-tetrafluoroethanes by isomerization of 1,2-dihalotetrafluoroethanes catalyzed by an active complex obtained "in situ" by reacting an anhydrous aluminium halide with the previously prepared isomer 1,1-dihalo-1,2,2,2-tetrafluoroethane, in an amount equal to at least 1 mole per mole of aluminium halide, in a medium consisting of 1,2-dihalotetrafluoroethane.

The halogen contained in a ratio of two atoms per mole in the utilized tetrafluoroethanes and the halogen contained in the aluminium halide are preferably selected from bromine and chlorine.

The isomerization reaction is preferably accomplished at the reflux temperature of 1,2-dihalotetrafluoroethane to be isomerized.

Active catalyst complexes prepared either from aluminium chloride or from aluminium bromide may be indifferently used.

The preparation of the active catalyst complex consists in adding to a mixture, consisting of small amounts of one of the two halides, i.e. anhydrous aluminium chloride or bromide, and of at least 10 parts by weight of 1,2-dihalotetrafluoroethane, an amount of previously prepared isomer 1,1-dihalotetrafluoroethane not lower than 1 mole per mole of aluminium halide.

As the aluminium halide it is possible to use any form of the anhydrous salt, commercially available in the form of granules or powder, or the compound prepared in situ by halogenation of metal aluminium.

The reaction which spontaneously occurs immediately after addition of the isomer 1,1-dihalotetrafluoroethane leads in a short time, comprised between a few minutes and approximately 1 hour, to the forming of a complex of unidentified chemical nature, which constitutes the activated form of the catalyst.

By simply bringing the complex, obtained "in situ" as explained hereinabove, into contact with great amounts of 1,2-dihalotetrafluoroethane, at temperatures ranging from 20° C. to the reflux temperature of the latter compound, the total conversion of 1,2-dihalotetrafluoroethane is attained with isomer 1,1-dihalotetrafluoroethane yields substantially higher than 80%.

The amount of 1,2-dihalotetrafluoroethane utilized in the preparation step of the activated form of the catalyst complex is not critical, but it is preferably when it is equal to 10 times by weight the aluminium halide amount, in order to moderate the exothermic reaction that develops when the previously prepared isomer, preferably in an amount not exceeding 500 times by weight, is introduced.

In the case of the isomerization of 1,2-dibromotetrafluoroethane, it may be operated according to the following procedure:

A small amount of anhydrous aluminium halide $AlBr_3$ or $AlCl_3$ is added with at least 10 parts by weight and preferably no more than 500 parts by weight, for each part by weight of halide, of $CF_2Br—CF_2Br$ and with an amount of $CF_3—CFBr_2$ equal to at least one mole per mole of aluminium halide. The mixture temperature is allowed to rise, in consequence of the exothermic reaction or of a slight heating, till reflux of the vapours accomplished by a reflux cooler.

The mixture is maintained at reflux, if necessary by means of a slight heating, until complete disappearance of $CF_2Br—CF_2Br$.

Under these conditions it is possible to convert in a short time from 200 to 500 parts by weight, for each part by weight of the initial aluminium halide, of $CF_2Br—CF_2Br$ with high yields of $CF_3—CFBr_2$.

As soon as the total amount of $CF_2Br—CF_2Br$ is converted, the mixture is washed with water and the organic phase, after separation, is distilled to isolate $CF_3—CFBr_2$ at a high purity degree.

In the event that, in the initial preparation step of the activated catalytic complex, an amount of $CF_2Br—CF_2Br$ lower than the one which can be completely converted, has been utilized, then further amounts of $CF_2Br—CF_2Br$ can be added after a time-period approximately ranging from 5 minutes to 1 hour from the introduction of isomer $CF_3—CFBr_2$.

SPECIFIC DESCRIPTION OF THE INVENTION

The following examples are given to better illustrate the present invention, without being however a limitation thereof.

EXAMPLE 1

Into a 1-liter flask equipped with a reflux cooler, whose top was connected with a $H_2SO_4$ valve, there were introduced in the order:
10 g of anhydrous $AlBr_3$,
95 g of 1,2-dibromotetrafluoroethane (Fluobrene, trademark registered in the name of Montedison),
23 g of 1,1-dibromotetrafluoroethane.

A spontaneous reaction started, which brought the mixture to the reflux temperature for about 5 minutes. On conclusion of the exothermy, 600 g of 1,2-dibromotetrafluoroethane were added, while maintaining the mixture under reflux conditions.

By subjecting to infrared analysis samples drawn from the reaction mixture it was possible to observe, after 20 minutes, the complete disappearance of the band at 9.9-10 microns typical of 1,2-dibromotetrafluoroethane, while an intense band at 11 microns, characteristic of 1,1-dibromo-tetrafluoroethane, was still present.

Successively, 1200 g of 1,2-dibromotetrafluoroethane were added in the aggregate in two successive steps and according to modalities analogous with those followed for the preceding addition. After about 40 minutes in the aggregate, on conclusion of the reaction, the mixture was cooled down to 10° C., it was washed with 200 ml of an aqueous solution at 3% of alkaline sulphite and the organic phase was separated.

By distillation of the organic phase, 1650 g of 1,1-dibromotetrafluoroethane, having a boiling point of 46° C. and being free from 1,2-dibromotetrafluoroethane, were obtained. That was equivalent to a yield of 86%.

EXAMPLE 2

By operating according to the same modalities of example 1, a flask was charged with:
10 g of anhydrous $AlBr_3$,
105 g of 1,2-dibromotetrafluoroethane,
27 g of 1,1-dibromotetrafluoroethane.

On conclusion of the exothermy, 5000 g of 1,2-dibromotetrafluoroethane were introduced in the aggregate and in one step. After about 3 hours and 15 minutes at reflux (such time being necessary to achieve the complete disappearance of 1,2-dibromotetrafluoroethane), the reaction mixture was treated as in example 1.

4385 g of 1,1-dibromotetrafluoroethane were obtained, the yield being equal to 85.6%.

EXAMPLE 3

Into the same apparatus as used in example 1, there were introduced, in the order:
7 g of anhydrous $AlBr_3$,
1300 g of 1,2-dibromotetrafluoroethane,
35.5 g of 1,1-dibromotetrafluoroethane.

The mixture was heated at reflux for 3 hours, a time necessary to observe, under the infrared analysis, the complete disappearance of 1,2-dibromotetrafluoroethane.

The mixture was then cooled to 10° C., it was washed with 170 ml of an aqueous solution at 3% of sodium sulphite.

After separation, the organic phase weighing 1275 g was analyzed by gas-chromatography; the following weight composition was obtained:
bromopentafluoroethane: 0.8% by weight
1,1-dibromotetrafluoroethane: 92% by weight
1,1,1-tribromotrifluoroethane: 7% by weight The 1,1-dibromotetrafluoroethane yield was slightly higher than 87%, such value having been confirmed by the amount of pure isomer (1170 g) obtained by successive distillation of the organic phase.

EXAMPLE 4

Example 3 was repeated, using as reagents:
7 g of anhydrous $AlBr_3$,
1300 g of 1,2-dibromotetrafluoroethane,
17 g of 1,1-dibromotetrafluoroethane.

An organic phase weighing 1250 g was obtained, which contained —as resulting from the gas-chromatographic analysis—90% by weight of 1,1-dibromotetrafluoroethane.

Such organic phase provided by distillation 1120 g of 1,1-dibromotetrafluoroethane with a yield of 85%.

EXAMPLE 5

Into the same apparatus as utilized in example 1, there were introduced, in the order:
3.5 g of anhydrous $AlCl_3$,
1350 g of 1,2-dibromotetrafluoroethane,
50 g of 1,1-dibromotetrafluoroethane.

The mixture was heated at reflux.

After 1 hour and 30 minutes a color change from light yellow to dark yellow was observed, and the infrared analysis revealed that the isomer had begun to form.

After about 50 minutes it was possible to observe, by infrared analysis, the complete disappearance of 1,2-dibromotetrafluoroethane.

It was then operated as described in example 3, thus obtaining 1335 g of organic phase which, on the gas-chromatographic analysis, revealed the following weight composition:
 bromopentafluoroethane: 1%
 unidentified compound: 1.2%
 1,1-dibromotetrafluoroethane: 92%
 1,1,1-tribromotrifluoroethane: 5%
The 1,1-dibromotetrafluoroethane yield was of 87.4%.

EXAMPLE 6 (comparative test)

Example 3 was exactly repeated, with the only exception that the 35.5 g of 1,1-dibromotetrafluoroethane were not added, i.e. no previously prepared isomer was added.

The mixture, after having been maintained at reflux for 3 hours, was subjected to the infrared analysis: it did not reveal any presence of the band at 11 microns, typical of isomer 1,1-dibromotetrafluoroethane, which proves that no appreciable reaction occurred.

We claim:

1. A process for isomerizing a 1,2-dihalotetrafluoroethane selected from the group consisting of 1,2-dichloro- and 1,2-dibromo-tetrafluoroethane to 1,1-dichloro- or 1,1-dibromo-1,2,2,2-tetrafluoroethane, said process being characterized in that the isomerization is catalyzed by an activated complex formed in situ, and obtained by reacting an anhydrous aluminum halide selected from the group consisting of aluminum chloride and aluminum bromide with preformed 1,1-dichloro- or 1,1-dibromo-1,2,2,2-tetrafluoroethane, in an amount equal to at least 1 mole per mole of aluminum halide, in a medium consisting essentially of 1,2-dichloro- or 1,2-dibromo-tetrafluoroethane, in an amount equal to 10 to 500 parts by weight with respect to the aluminum halide, the isomerization being carried out at the reflux temperature of the 1,2-dichloro- or 1,2-dibromo-tetrafluoroethane to be isomerized.

* * * * *